United States Patent
Langhorn et al.

(10) Patent No.: US 10,070,959 B2
(45) Date of Patent: Sep. 11, 2018

(54) METHOD OF TEXTURING PROSTHETIC IMPLANTS

(71) Applicant: DEPUY SYNTHES PRODUCTS, INC., Raynham, MA (US)

(72) Inventors: Jason B. Langhorn, Warsaw, IN (US); Gary R. Fernandes, Assonet, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 70 days.

(21) Appl. No.: 15/278,498

(22) Filed: Sep. 28, 2016

(65) Prior Publication Data
US 2018/0085221 A1    Mar. 29, 2018

(51) Int. Cl.
*B24C 1/08*  (2006.01)
*B24B 31/03*  (2006.01)
(Continued)

(52) U.S. Cl.
CPC .......... *A61F 2/30767* (2013.01); *A61F 2/30* (2013.01); *A61F 2/30771* (2013.01); *A61F 2/36* (2013.01);
(Continued)

(58) Field of Classification Search
CPC ......... B24C 1/08; B24B 11/00; B24B 31/003; B24B 31/03; B24B 31/14; A61F 2/30;
(Continued)

(56) References Cited

U.S. PATENT DOCUMENTS 5,211,833 A * 5/1993 Shirkhanzadeh ... A61F 2/30767
                                                                    205/322
5,308,412 A    5/1994 Shetty
(Continued)

FOREIGN PATENT DOCUMENTS

CN           102921037 A  *  2/2013

OTHER PUBLICATIONS

Paul, J.P., Forces Transmitted by Joints in the Human Body, Lubrication and Wear in Living and Artificial Human Joints, The Institution of Mechanical Engineers, Proc. Inst. Mech. Eng. Part 3J, 181: 8-15, 1967.
(Continued)

*Primary Examiner* — Eileen Morgan (57) ABSTRACT

A method of treating an articular surface of a metal orthopedic implant includes polishing the surface, blasting the surface with a blast media after the first polishing step and polishing the blasted surface of the metal orthopedic implant after the blasting step. The blasting step roughens the surface to create a surface skew $R_{sk}/S_{sk}$ defined by peaks and valleys. The second polishing step reduces the surface skew to a negative skew $R_{sk}/S_{sk}$ and produces an average roughness $R_a/S_a$ that is acceptable. Lubrication at the interface of the treated articular surface and the corresponding bearing articular surface is improved, thereby improving wear resistance. Both polishing steps may be performed by drag finishing the surface through an abrasive media.

19 Claims, 7 Drawing Sheets

(51) Int. Cl.
   *A61F 2/30*  (2006.01)
   *A61F 2/36*  (2006.01)
   *A61F 2/38*  (2006.01)
   *A61F 2/40*  (2006.01)
   *B24B 31/00* (2006.01)
   *B24C 3/32*  (2006.01)

(52) U.S. Cl.
   CPC ............ *A61F 2/389* (2013.01); *A61F 2/3859* (2013.01); *A61F 2/4014* (2013.01); *A61F 2/4081* (2013.01); *B24B 31/003* (2013.01); *B24B 31/03* (2013.01); *B24C 1/08* (2013.01); *B24C 3/32* (2013.01); *A61F 2002/30906* (2013.01); *A61F 2310/00023* (2013.01); *A61F 2310/00029* (2013.01)

(58) Field of Classification Search
   CPC ........ A61F 2/30767; A61F 2002/30906; A61F 2310/00023; A61F 2310/00029
   USPC .................................. 451/34, 35, 38, 57, 66
   See application file for complete search history.

(56) References Cited

U.S. PATENT DOCUMENTS

| | | | |
|---|---|---|---|
| 5,560,096 A * | 10/1996 | Stephens | A61F 2/3859 29/527.6 |
| 5,681,205 A * | 10/1997 | Yam | B08B 3/06 450/40 |
| 5,728,748 A | 3/1998 | Sun | |
| 5,746,272 A | 5/1998 | Mastrorio | |
| 5,879,400 A | 3/1999 | Merrill | |
| 5,906,234 A * | 5/1999 | Mastrorio | A61F 2/30771 164/34 |
| 6,017,975 A | 1/2000 | Saum | |
| 6,025,536 A * | 2/2000 | Bender | A61F 2/30767 623/23.53 |
| 6,183,353 B1 * | 2/2001 | Frantzen | A61F 2/91 451/104 |
| 6,228,900 B1 | 5/2001 | Shen | |
| 6,242,507 B1 | 6/2001 | Saum | |
| 6,245,276 B1 | 6/2001 | McNulty | |
| 6,281,264 B1 | 8/2001 | Salovey | |
| 6,316,158 B1 | 11/2001 | Saum | |
| 6,537,202 B1 | 3/2003 | Frantzen | |
| 6,911,249 B2 | 6/2005 | Wagner | |
| 7,771,485 B2 | 8/2010 | Grundei | |
| 7,892,071 B2 * | 2/2011 | Ernsberger | A61F 2/30767 451/37 |
| 7,959,490 B2 * | 6/2011 | Sutton | A61F 2/30767 451/5 |
| 8,323,349 B2 | 12/2012 | Schmid | |
| 8,444,914 B2 | 5/2013 | Fecher | |
| 8,449,347 B2 | 5/2013 | Sutton | |
| 8,580,134 B2 | 11/2013 | Tong et al. | |
| 9,849,019 B2 * | 12/2017 | Miller | A61F 5/01 |
| 2003/0212161 A1 | 11/2003 | McKellop | |
| 2007/0293647 A1 | 12/2007 | McKellop | |
| 2009/0192464 A1 * | 7/2009 | Axelsson | A61F 5/445 604/164.04 |
| 2011/0012478 A1 * | 1/2011 | Najafi | B81C 1/0019 310/334 |
| 2011/0166670 A1 * | 7/2011 | Lyngstadaas | A61L 27/06 623/23.53 |
| 2013/0189905 A1 | 7/2013 | Toni et al. | |
| 2013/0282104 A1 * | 10/2013 | Bayer | A61L 31/022 623/1.15 |
| 2015/0093283 A1 * | 4/2015 | Miller | A61F 2/3859 419/55 |
| 2015/0148910 A1 | 5/2015 | Raeymaekers | |
| 2015/0151399 A1 | 6/2015 | Seeley et al. | |
| 2016/0213477 A1 | 7/2016 | Slocum, Jr. | |
| 2016/0339144 A1 * | 11/2016 | McEntire | A61L 27/10 |
| 2017/0143495 A1 * | 5/2017 | Dunn | A61F 2/34 |
| 2017/0197014 A1 * | 7/2017 | McEntire | A61L 27/06 |
| 2017/0249440 A1 * | 8/2017 | Lang | G06F 19/3437 |
| 2017/0348107 A1 * | 12/2017 | Lee | A61F 2/30771 |

OTHER PUBLICATIONS

Effects of COCRMO Surface Finishing on UHMWPE Wear in a Pin-On-Disk Test, Hippensteel, et al; Orthopaedic Research Society Annual Meeting, Mar. 28-31, 2015—1 Page.
Wet Blast Articulation Surfaces for Total Knee Replacement Components, Metcalfe, et al, Depuy Synthes Joint Reconstruction, Apr. 12-16, 2015—1 Page.
Rosler, Compact Drag Finisher, Pub. No. GB 250-07, Available by Sep. 28, 2016, 3 Pages, www.rosler.com.
European Search Report for Corresponding Application No. EP 17192544.9-1016, dated Feb. 22, 2018, 6 Pages.

* cited by examiner

METHOD OF TEXTURING PROSTHETIC IMPLANTS

TECHNICAL FIELD

The present disclosure relates generally to orthopaedic prostheses, and more particularly to a method of preparing the articulating surface of one of the components of an orthopaedic implant system.

BACKGROUND

Movement of the joints of human musculoskeletal system involves movements of adjacent bones through various ranges of motion. For example, movement of the human knee involves movements of the femur, tibia and the patella. Specifically, during flexion and extension, the distal end of the femur and the proximal end of the tibia articulate relative to one another through a series of complex movements as the patella articulates with the femur. Similarly, movement of the human hip involves movements of the femur with respect to the acetabulum, and movement of the shoulder involves movement of the humerus with respect to the glenoid. Damage (e.g., trauma) or disease can deteriorate the bones, articular cartilage, and ligaments of the bones associated with these joints, which can ultimately affect the ability of the natural joint to function properly. As a result, orthopaedic prostheses have been developed and implanted into surgically prepared ends of the bones of the joints to provide greater mobility for the patient.

Figure 1:
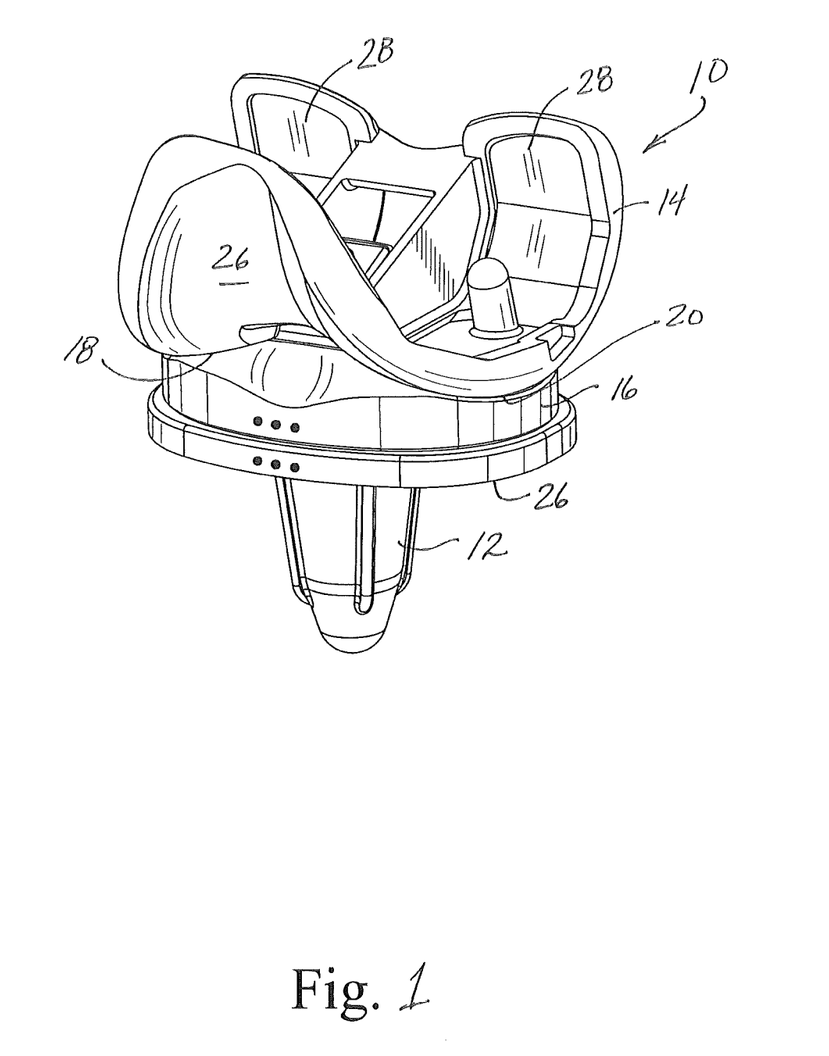
FIG. 1 is a perspective view of an example of an orthopaedic knee prosthesis system.
Figure 2:
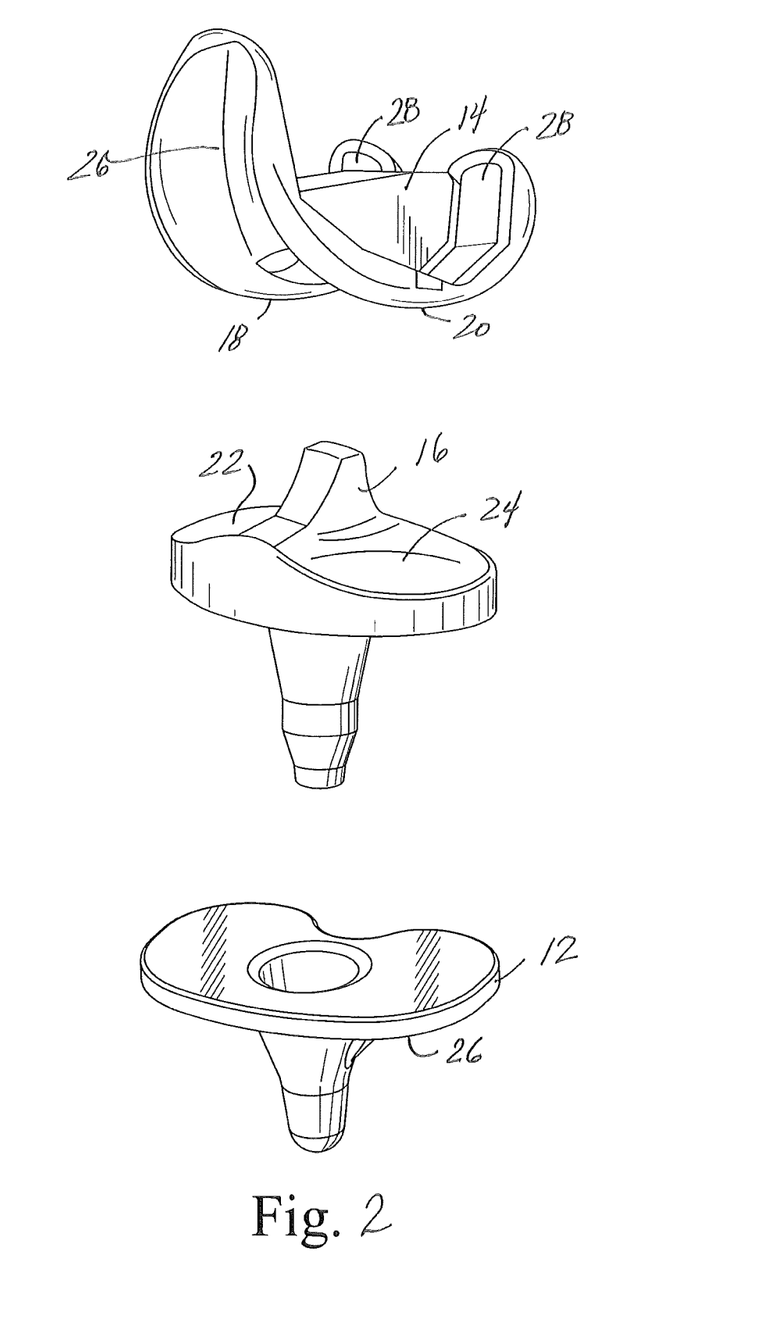
FIG. 2 is an exploded view of the knee prosthesis system of FIG. 1.

For example, a typical orthopaedic prosthesis 10 for a total knee replacement is shown in FIGS. 1 and 2. The illustrated prosthesis includes a tibial component 12 or tibial tray to be coupled to the patient's proximal tibia, a femoral component 14 to be coupled to the patient's distal femur, and a bearing component (or tibial insert) 16 positioned between the tibial tray and the femoral component.

Once implanted, articular surfaces 18, 20 on the femoral component bear and articulate against articular surfaces 22, 24 on the proximal surface of the tibial insert 16 as the knee is moved through flexion and extension. A groove on the femoral component 14 provides a third articular surface 26 that articulates against a bearing surface on a patellar implant component (not shown) as the knee is flexed and extended. Other surfaces 26, 28 of the implants 12, 14 face the bone when implanted, and may have cement pockets or textured surfaces to encourage bone ingrowth.

Figure 3:
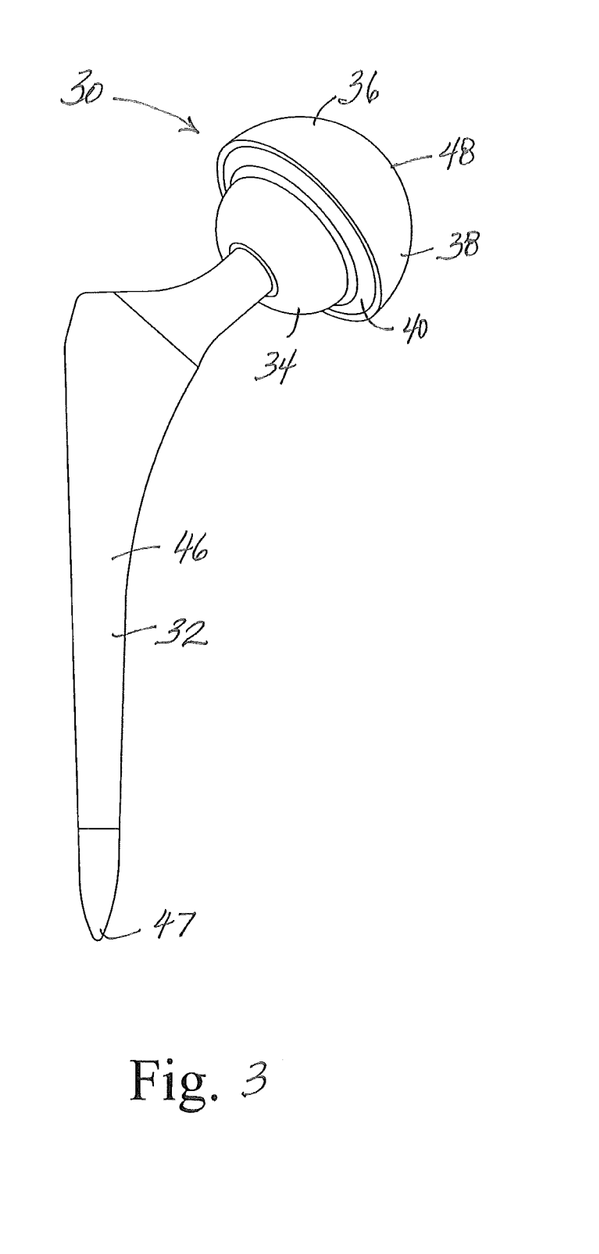
FIG. 3 is a perspective view of an example of an orthopaedic hip prosthesis system.
Figure 4:
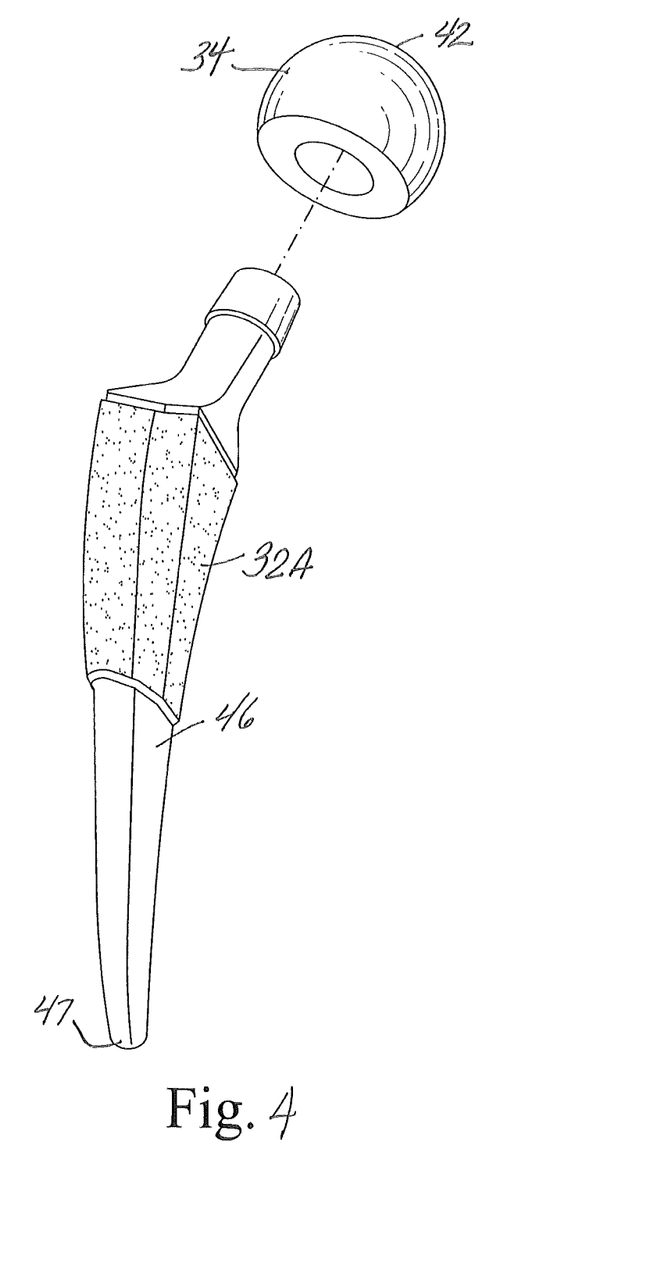
FIG. 4 is an exploded perspective view of a femoral stem and femoral head of an example of an orthopaedic hip prosthesis system.
Figure 5:
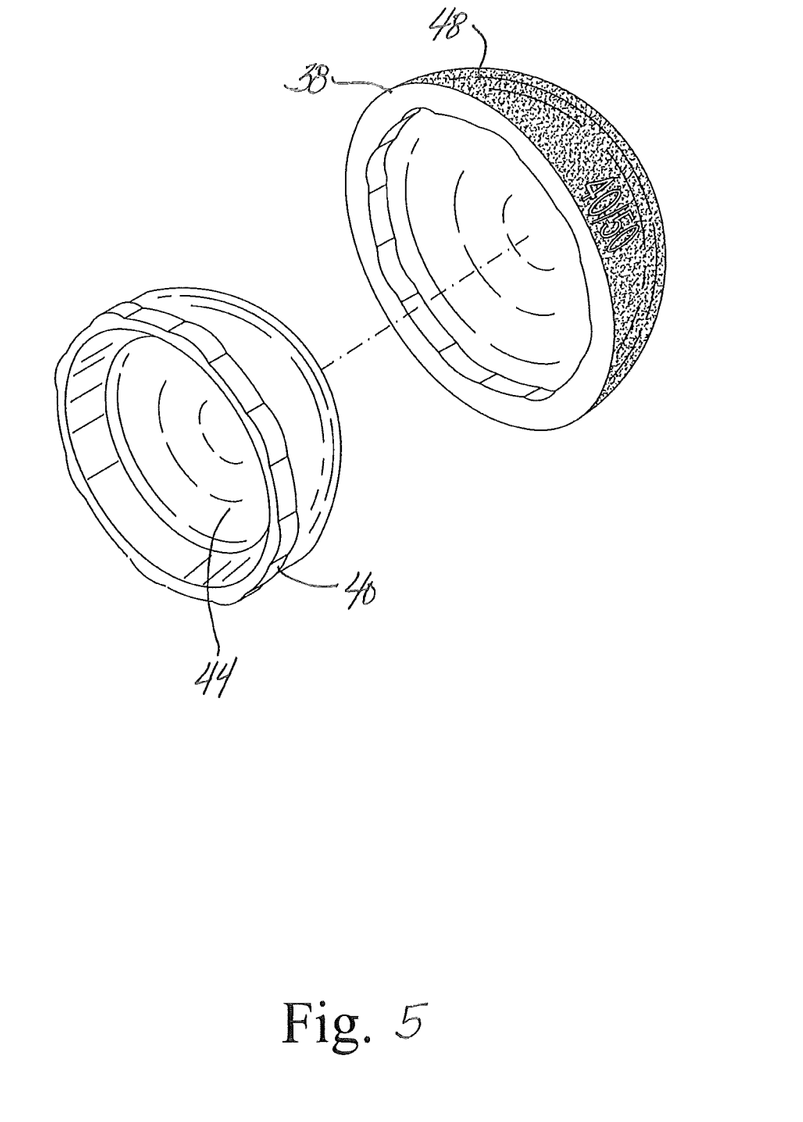
FIG. 5 is an exploded view of an example of an acetabular cup and liner for use in an orthopaedic hip prosthesis system.

A typical orthopaedic prosthesis 30 for hip replacement is shown in FIGS. 3-5. The hip prosthesis 30 includes a metal stem 32 and metal femoral head 34 and an acetabular implant assembly 36 including an acetabular cup 38 and a bearing component (acetabular liner) 40 fixed to the acetabular cup 38 and receiving the femoral head 34.

In the embodiment illustrated in FIG. 4, the stem 32A has some differences compares to the stem 32 of FIG. 3. In both, the femoral implant is modular, comprising an assembly of a stem 32 or 32A component with a femoral head component 34. The head component 34 defines a curved articular surface 42 that is received within and articulates against a concave articular surface 44 of the acetabular liner 40. The majority of the length of the stem 32 defines a bone-facing surface 46 extending proximally from the distal end 47 bears against and faces the bone (proximal femur). The exterior surface of the cup 38 also defines a bone-facing surface 48.

Figure 6:
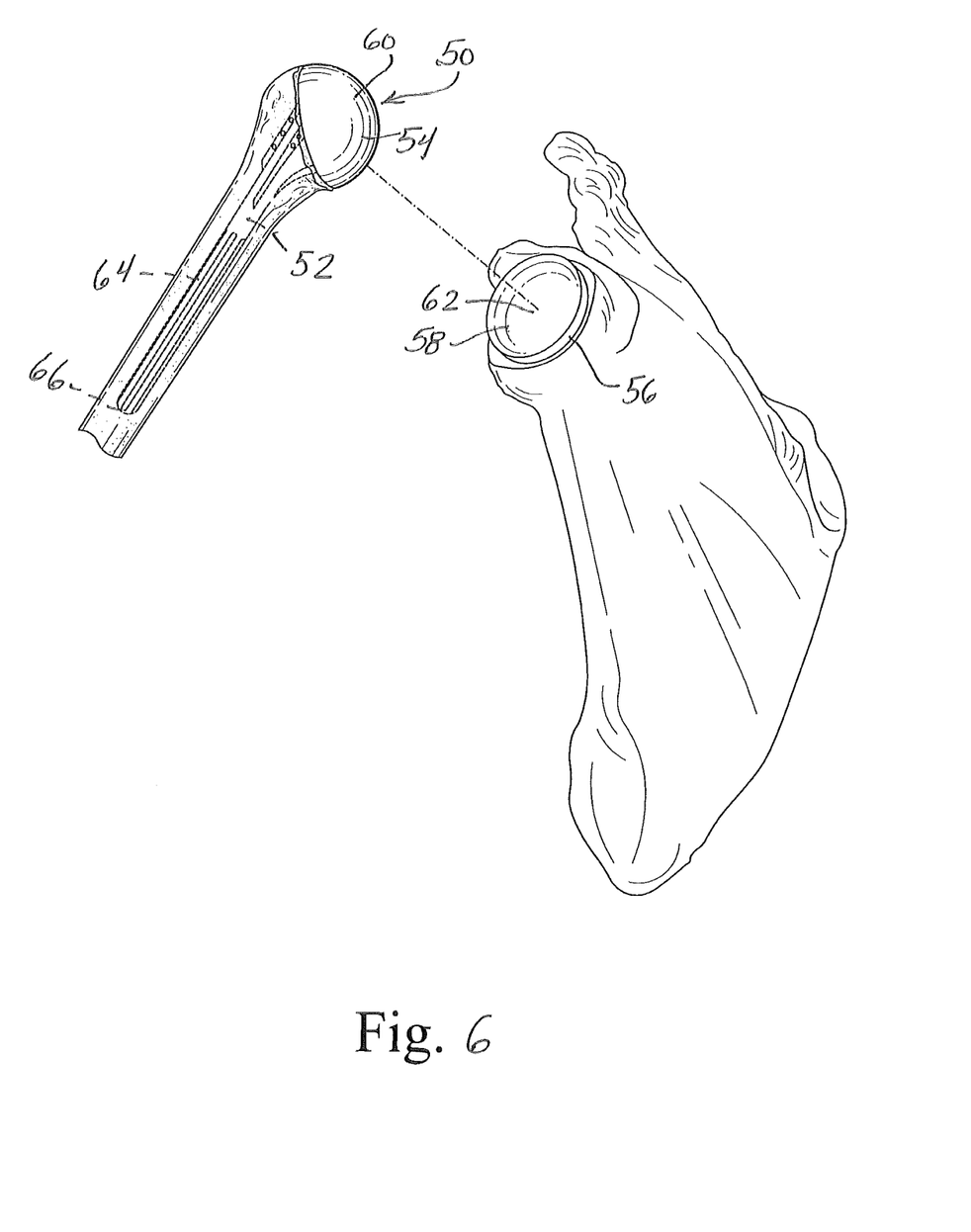
FIG. 6 is perspective view of an example of an orthopaedic shoulder prosthesis system, shown implanted on a humerus and shoulder.

A typical orthopaedic prosthesis 50 for shoulder replacement is illustrated in FIG. 6. includes a metal stem 52 and metal humeral head 54 and a glenoid component 56. Common glenoid components 56 include a metal portions and a bearing 58 fixed to the metal portion and receiving or articulating against the humeral head 54. The head component 54 defines a convex curved articular surface 60 that is received within and articulates against a concave curved articular surface 62 of the bearing 58. The majority of the length of the stem 52 defines a bone-facing surface 64 extending proximally from the distal end 66 and bears against and faces the bone (proximal humerus). The exterior surface of the glenoid component also defines a bone-facing surface. FIG. 6 illustrates the shoulder prosthesis 50 implanted in the proximal humerus and glenoid.

In such typical orthopaedic prostheses, the tibial tray 12, distal femoral component 14, femoral stem 32, femoral head 34, acetabular cup 38, humeral stem 52, humeral head 54 and part of the glenoid component 56 are typically made of metal, such as a cobalt chrome alloy or a titanium alloy (such as titanium alloy Ti-6Al-4V, for example). The bearing component (tibial insert 16, acetabular liner 40 or glenoid bearing 58) is typically made of a polymer, or in the case of hip prostheses, may comprise a metal or ceramic liner. In some cases, the entire tibial component and entire glenoid component may comprise a polymer.

The polymer used for the bearing components 16, 40, 58 may be ultrahigh molecular weight polyethylene (UHMWPE). The UHMWPE may comprise a cross-linked material, for example. Techniques for crosslinking, quenching, or otherwise preparing UHMWPE are described in numerous issued U.S. patents, examples of which include: U.S. Pat. No. 5,728,748 (and its counterparts) issued to Sun, et al.; U.S. Pat. No. 5,879,400 issued to Merrill et al.; U.S. Pat. No. 6,017,975 issued to Saum, et al.; U.S. Pat. No. 6,242,507 issued to Saum et al.; U.S. Pat. No. 6,316,158 issued to Saum et al.; U.S. Pat. No. 6,228,900 issued to Shen et al.; U.S. Pat. No. 6,245,276 issued to McNulty et al.; and U.S. Pat. No. 6,281,264 issued to Salovey et al. The disclosure of each of these U.S. patents is incorporated by reference herein in their entireties. The UHMWPE of the bearing material may be treated to stabilize any free radicals present therein, such as through the addition of an antioxidant such as vitamin E. Techniques for stabilizing UHMWPE with antioxidants are disclosed, for example, in U.S. Pat. Pub. No. 20070293647A1 (Ser. No. 11/805,867) and U.S. Pat. Pub. No. 20030212161A1 (Ser. No. 10/258,762), both entitled "Oxidation-Resistant And Wear-Resistant Polyethylenes For Human Joint Replacements And Methods For Making Them."

Each of these implant systems share some common characteristics: an articulation surface 18, 20, 26, 42, 60 of one implant component 14, 34, 54 (usually metal or ceramic) bears and articulates against an articular surface 22, 24, 44, 62 of a bearing component 16, 40, 56. Over years of repeated use, the repeated articulation of these components against one another can lead to wear of the bearing component 16, 40, 56. Excessive wear of the bearing component can lead to issues requiring that the prosthetic joint be removed and replaced with another prosthetic implant in a revision procedure.

To address wear, various solutions have been proposed. For example, attempts have been made to reduce wear by optimizing the polishing of the metal articulating surface(s) to a high gloss. Such polishing processes can however be costly. Some have suggested providing a textured surface through etching or anodizing to contain a biological fluid to improve lubrication. See, for example, WO2015/034471A1.

SUMMARY

The present invention addresses the goal of improving wear performance of orthopaedic implant prostheses in a cost effective manner.

According to one aspect, the present invention addresses this goal by providing a method of treating the articulation surface of an orthopaedic implant comprising polishing the articulation surface of the orthopaedic implant, blasting the polished surface of the implant followed by polishing the blasted surface.

In a particular embodiment, the step of polishing the articulation surface comprises drag finishing the articulation surface through an abrasive media. Similarly, the step of polishing the blasted surface may comprise drag finishing the blasted surface through an abrasive media.

The blasting step is performed with a blasting media. In a particular embodiment, the blasting step comprises wet blasting. The wet blasting step may be performed with a spherical bead media having a size in the range of 125-180 um (B100) or 0-125 um (B125), a media concentration in the range of 15-25% by volume, and with a pressure of 30-40 psi. In this embodiment, the blasting step increases the roughness of the surface of the metal orthopaedic implant.

In a more particular embodiment, the polishing step before blasting is longer than the polishing step after blasting.

In any of these embodiments, the articulation surface of the orthopaedic implant component has a negative surface skew ($R_{sk}$, $S_{sk}$) after the second polishing step.

In another more particular embodiment, the first polishing step comprises drag finishing the articulation surface through an abrasive media for a first period of time and the step of polishing the blasted surface comprises drag finishing the blasted surface through an abrasive media for a second period of time. In these embodiments, the first period of time may be a maximum of 40 minutes and the second period of time may be a maximum of 20 minutes. The maximum time periods may be higher for different starting conditions of material and types of material or alloy used.

In any of these embodiments, the abrasive media used for the first drag finishing step may comprise plastic ceramic composite, and the abrasive media used for the second drag finishing step may comprise nutshell or corncob bonded with a ceramic polishing media.

In any of these embodiments, the blasting step may create a surface having a surface roughness ($R_a$/$S_a$) and skew ($R_{sk}$/$S_{sk}$) defined by a plurality of peaks and valleys and the second polishing step reduces roughness ($R_a$/$S_a$) and increases the negative skew $R_{sk}$/$S_{sk}$ of the surface. The surface skew $R_{sk}$/$S_{sk}$ may be from −1 to −3, for example, after the second drag finishing step. The average surface roughness after the second polishing step may be less than 0.1 microns. Surface characteristics (roughness and skew) may be measured by white light interferometry.

In any of these embodiments, the articulation surface of the orthopaedic implant may comprise a metal, such as a standard cobalt-chrome alloy or a titanium alloy.

In any of these embodiments, the orthopaedic implant may comprise a distal femoral component or a tibial tray of a knee implant, a femoral head of a hip implant, or a humeral head or glenoid component of a shoulder implant.

BRIEF DESCRIPTION OF THE DRAWINGS

The background and detailed description particularly refer to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, proximal, distal, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Terms related to the characterization of surface roughness may be used throughout their disclosure. For example, average surface roughness $R_a$, $S_a$ and surface skew $R_{sk}$, $S_{sk}$ are used. Use of these terms is intended to be consistent with their well-understood meanings unless noted otherwise. In addition, standard methods of measuring and/or characterizing surface textures, and standard equipment used in measuring and/or characterizing surface textures are intended to be usable with respect to the present invention unless expressly excluded.

Although the results below are reported as three-dimensional results ($S_a$ and $S_{sk}$), it should be understood that the results should be comparable for 2-dimensional measurement ($R_a$ and $R_{sk}$). References to specific values of surface roughness and skew should be understood to refer to either $S_a$ and $R_a$ and $S_{sk}$ and $R_{sk}$ unless otherwise specifically called out.

In the process of the present invention, the starting point is a standard orthopaedic implant component that has an articulating surface, such as a distal femoral component 14, a femoral head 34 or a humeral head 54, for example. The implant may be made of a standard metal, such as a standard CoCrMo alloy or titanium alloy used in orthopaedic implants (although the invention is not limited to any particular alloy unless expressly called for in the claims). It should be understood that these implant components are identified as examples, only; the invention is not limited to these components unless expressly called for in the claims. It is also expected that the principles of the present invention could be applied to ceramic orthopaedic implant components, such as ceramic femoral heads, for example.

In general, the process of the present invention involves polishing the articulation surface of the implant component, blasting the polished surface and then polishing the blasted surface.

As used herein, "polishing" refers to any standard abrasive manufacturing process that removes material from the surface being polished to reduce the roughness of the surface being polished. Standard polishing processes include, for example, vibratory finishing in an abrasive media and tumbling in an abrasive media. In the case of the examples below, drag finishing the articulation surface with an abrasive media has proven to be an effective means of polishing the articulation surface.

In contrast, "blasting" refers to a surface treatment that deforms the surface rather than removes material from the surface. Generally, blasting refers to propelling a media under pressure to at the surface to work the surface. In the case of the examples below, blasting the polished articulation surface creates valleys and peaks in the surface through plastic deformation. The peaks are removed in the final polishing step through abrasion to yield a surface with an acceptable surface roughness and a negative skew.

The implant component may first be mounted on a fixture and placed into a vessel containing an abrasive drag finishing media. For example, a plastic abrasive media such as Rosler RKH 4 (polyester resin/ceramic media composite) may be used. The mounted implant component is submerged and then moved through the abrasive media in a planetary motion. For example, the implant component may be revolved around an axis as the fixture itself is revolved to move the implant component through the media (which may itself be in a revolving vessel). This step will polish the implant component before it is further textured in a wet blasting process. For example, the implant component may have an average surface roughness $R_a/S_a$ of 0.03 μm after being dragged through the composite media for up to 40 minutes. The length of time of the first polishing step may vary depending on the starting conditions of the material and the type of material or alloy used.

After this first polishing step, the implant component may again be held by a fixture and then blasted to further roughen the desired surface. For example, a wet blasting process may be used, with a pressurized blasting media slurry (for example, Zirblast B100 or Microblast B125 size zirconia media in water 15-25% by volume at a pressure of 30 or 40 psi) applied to the desired surface for a controlled time (for example, 1 minute). This step will further roughen the articulating surface of the implant component by creation of a plurality of peaks and valleys.

The surface roughness of the implant component after blasting can be characterized as comprising a plurality of peaks and valleys, creating a surface roughness that has an $R_a$, for example, of 0.3 μm and an $R_{sk}$ of 0 to −1.

To reduce or eliminate the peaks generated by the blasting step, while retaining the valleys created, the blasting step may be followed by another drag finishing or polishing step. For example, the implant component, held by a suitable fixture, may be immersed in another abrasive drag media (such as Rosler Supervelat corncob polishing media, a corncob based media comprising corncob bonded with a ceramic polishing media, www.rosler.us; Rösler Oberflächentechnik GmbH) and dragged through the media for a period of time and at a speed that will remove or substantially remove the peaks. Such a processing step can be expected to reduce the average roughness $R_a/S_a$ and create a more negative surface skew $R_{sk}/S_{sk}$.

Throughout the polishing and blasting steps, the surfaces of the implant component that are exposed to the abrasive polishing media and blasting media may be controlled so that only the articulating surfaces (such as surfaces 18, 20 of femoral component 14, surface 42 of head 34 or surface 60 of head 54) are exposed. Because it is frequently desirable that the bone-facing surfaces have different surface characteristics, surfaces 26, 28, 46, 48, 64 may be protected from exposure to the media if desired, through masking or by the structure of the fixture holding the components.

The drag finishing and blasting steps may be performed using commercially available equipment. For example, suitable equipment for the drag finishing steps is available from Rosler Metal Finishing (www.rosler.us; Rösler Oberflächentechnik GmbH). This equipment allows for multiple implant components to be mounted on individual spindles, which are in turn mounted on a carousel so that the spindles and carousel may be rotated to move the components through a bowl of abrasive material (the bowl may also be rotated). Suitable equipment for the blasting step is available from Rösler Metal Finishing (www.rosler.us; Rösler Oberflächentechnik GmbH) such as the RWB 48 abrasive wet blasting cabinet.

The abrasive media used in the process may be standard grinding or polishing media used in the manufacture of medical devices, selected according to the stage of the process. For example, the abrasive media can comprise commercially available nutshell or corncob based particles and composites of such particles with other materials such as ceramics. "Nutshell or corncob based polishing media" is intended to include commercially available media where nutshell or corncob is bonded with another material such as ceramic. As used herein, "abrasive media" is intended to encompass these media, as well as other standard materials used in conventional polishing processes. The polishing step can be a wet or dry step. The particular characteristics of the abrasive media used can be selected to produce the desired surface finish properties. Other parameters in the polishing steps (such as speed of rotation of the elements that rotate and drag time) can be adjusted to produce the desired surface finish properties.

Similarly, the blast media used in the process may be standard blast media. For example, a slurry of zirconia based ceramic beads ("Zirblast", Saint Gomain, Worcester, Mass.) in water can be used. As used herein, "blast media" is intended to encompass ceramic, glass and metal beads, as well as other standard materials used in conventional blast processes. The blast process can be a wet or dry process. The particular characteristics of the blast media and the parameters of the blast process (such as pressure and time) can be adjusted to produce the desired surface finish properties.

To compare the process of the present invention to the prior art polishing process, sample CoCrMo disks were prepared as set forth in the following table (all of the samples were cast CoCrMo disks, ASTM F75, heat treated [HIP and Homogenized]):

| Sample group | Surface Finish Description | Process Parameters | | |
|---|---|---|---|---|
| 1 | Highly Polished | Manually polished to a mirror finish | | |
| 2 | Blasted + 2 Stage Polish | Plastic based Media Drag for <40 minutes (speed: outer carousel at 32 rpm, inner spindle at 20 rpm) | Wet blast Zirblast B100 (125-180 μm) media size at 40 psi for 3 minutes | Nutshell based media Drag for 10 minutes (speed: outer carousel at 32 rpm, inner spindle at 20 rpm) |
| 3 | Blasted + 2 Stage Polish | Plastic based Media Drag for <30 minutes (speed: outer carousel at 32 rpm, inner spindle at 20 rpm) | Wet blast B125 (0-125 μm)_media size at 30 psi for 1 minute | Nutshell based media Drag for 4 minutes (speed: outer carousel at 32 rpm, inner spindle at 20 rpm) |
| 4 | 2 Stage - Polish and Blast | Plastic based media Drag for 30 minutes (speed: outer carousel at 32 rpm, inner spindle at 20 rpm) | Wet blast B125 (0-125 μm)_media size at 40 psi for 1 minute | — |
| 5 | 2 Stage Drag | Ceramic based media Drag for 100 minutes (speed: outer carousel at 32 rpm, inner spindle at 20 rpm) | Plastic Media Drag for 64 minutes (speed: outer carousel at 32 rpm, inner spindle at 20 rpm) | — |
| 6 | 3 Stage Polish | Ceramic based media Drag for 100 minutes (speed: outer carousel at 32 rpm, inner spindle at 20 rpm) | Plastic Media Drag for 64 minutes (speed: outer carousel at 32 rpm, inner spindle at 20 rpm) | Nutshell based media Drag for 44 minutes (speed: outer carousel at 32 rpm, inner spindle at 20 rpm) |

The plastic-based abrasive media used in the first polishing step in samples 2-4 above was Rosler RKH 4 (polyester resin/ceramic media composite). This same material was used in the plastic media drag steps for samples 5 and 6. The nutshell based media used in samples 2, 3 and 6 was Rosler Polishing Grain SVK-747.

Figure 7:
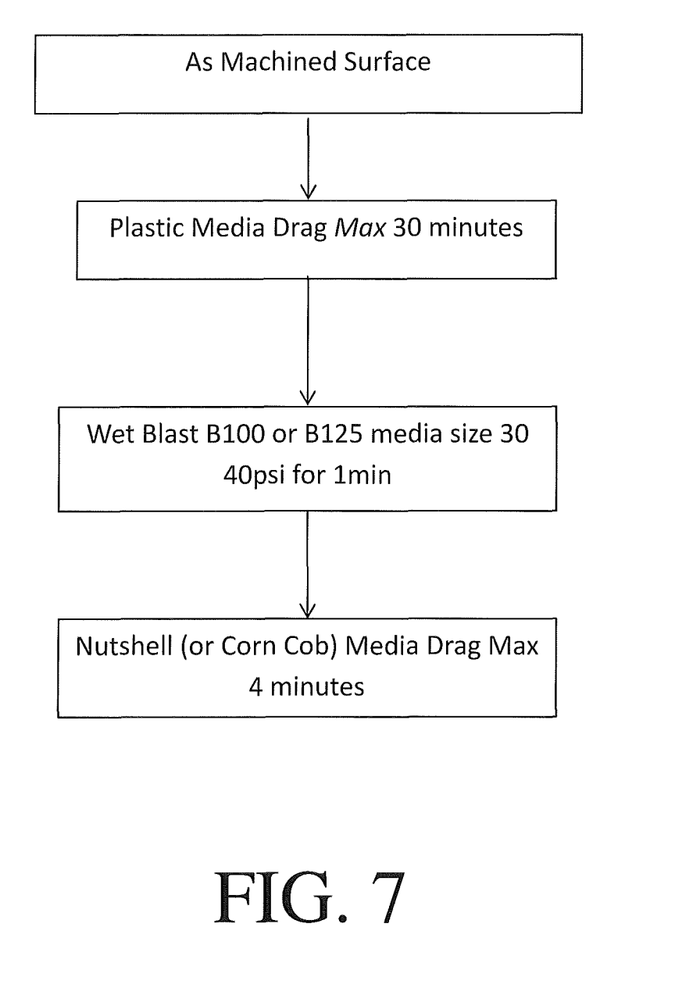
FIG. 7 is a flow chart of process steps for finishing the articular surface of one or more of the metal components of an orthopaedic prosthesis system, such as the systems shown in FIGS. 1-6.

FIG. 7 illustrates the process steps for sample 3.

As set forth below, surfaces of the samples identified above were characterized to determine $S_a$ and $S_{sk}$, and a pin on disk wear test was also performed. The surface characterization was done using white light interferometry (Zygo NewView 5000, Middlefield, Conn.). Pin-on-disk wear testing was performed using an OrthoPOD pin-on-disk tribometer (AMTI, Watertown, Mass.) under variable load and articulation representative of a Paul curve (Paul, Proc. Inst. Mech. Eng. 181, 8-15, 1967) with a peak load of 330N for 1.98 MCyc. The pin-on-disk test was performed using bovine serum (64.8 mg/mL total protein concentration; HyClone Laboratories Inc., Logan, Utah) at 37±2° C. supplemented with sodium azide and EDTA. Pins were cleaned, weighed and gravimetric wear rates determined six times throughout the course of the test using linear regression in accordance with ISO 14242-2:2000(E) with soak compensation. Wettability (contact angle) was measured using a Kruss drop shape analysis system (DSA 10), and 10 μl water droplets. The metal components were articulated against parts comprising the DePuy Synthes Joint Reconstruction commercial XLK UHMWPE. This UHMWPE material is made from a GUR 1020 resin irradiated to 50 kGy and remelted.

| Sample group | Average Surface roughness $S_a$ before Pin-on-disk testing (μm) | Average Surface roughness $S_a$ After Pin-on-disk testing (μm) | Skew $S_{sk}$ | Average Wear Rate mg/Mcyc | Average Wettability (contact angle) |
|---|---|---|---|---|---|
| 1 | 0.02 | 0.03 | +1.0 (±0.5) | 7.2 | 98 |
| 2 | 0.06 | 0.07 | −2.2 (±0.8) | 3.4 | 68 |
| 3 | 0.04 | 0.05 | −1.2 (±0.4) | 3.6 | 65 |
| 4 | 0.2 | 0.25 | 0 (±0.8) | 7.0 | 75 |
| 5 | 0.02 | 0.035 | 0 (±0.3) | 7.3 | 70 |
| 6 | 0.02 | 0.04 | +1.0 (±0.5) | 7.2 | 95 |

For some samples, surface roughness was also characterized during the process. For example, in Sample group 2, $S_a$ and $S_{sk}$ were measured after the blasting step as 0.32 μm and 0.8, respectively.

Sample groups 2 and 3 had $S_a$ values within the 0.1 micron specification called out in ISO 21534. For sample groups 2 and 3, the $S_{sk}$ values were negative after the final surface finishing step. These samples also exhibited lower water droplet contact angles and wear rates compared to the highly polished control sample 1. These negative skew values indicate that the surface contained pockets that are believed to capture lubricant at the bearing surfaces to improve hydrodynamic lubrication. These pockets can also be expected to entrap potentially harmful wear particulates. It is also expected that these samples will exhibit faster start-up lubrication in vivo.

The above-described processes can be applied to implant components. For example, the articulating surfaces of a tibial tray 12, femoral component 14, femoral head 34, or humeral head 54 can be finished using the process of the present invention, and it is anticipated that these implant components will exhibit improved wear performance against the articular surfaces of their associated bearings 16, 40, 58.

Accordingly, the process of the present invention is expected to improve the wear performance of orthopaedic prostheses in a cost effective manner.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

We claim:

1. A method of treating an articulation surface of an orthopaedic implant comprising the following steps carried out in order:
   a first step of polishing the articulation surface of the orthopaedic implant;
   a second step of blasting the polished surface of the orthopaedic implant; and
   a third step of polishing the blasted surface of the orthopaedic implant;
   wherein:
   the first step of polishing the articulation surface of the orthopaedic implant comprises drag finishing the articulation surface of the orthopaedic implant with an abrasive media for a first period of time;
   the third step of polishing the blasted surface of the orthopaedic implant comprises drag finishing the blasted surface of the orthopaedic implant with an abrasive media for a second period of time; and
   wherein the second period of time is less than the first period of time.

2. The method of claim 1 wherein blasting comprises wet blasting.

3. The method of claim 1 wherein the first polishing step before blasting is longer than the third polishing step after blasting.

4. The method of claim 1 wherein the articulation surface of the orthopaedic implant has a negative surface skew ($S_{sk}$) after the second polishing step.

5. The method of claim 1 wherein the first period of time is a maximum of 40 minutes.

6. The method of claim 1 wherein the second period of time is a maximum of 20 minutes.

7. The method of claim 1 wherein the abrasive media used in the first drag finishing step comprises a plastic ceramic composite.

8. The method of claim 1 wherein the abrasive media used in the second drag finishing step comprises nutshell or corncob based polishing media.

9. The method of claim 1 wherein the blasting step creates a surface having a surface skew defined by a plurality of peaks and valleys and the second drag finishing step creates a surface having a negative skew.

10. The method of claim 1 wherein the articulation surface of the orthopaedic implant has a surface skew of from −1 to −3 after the second drag finishing step.

11. The method of claim 1 wherein the articulation surface of the orthopaedic implant has an average surface roughness of less than 0.1 microns after the second drag finishing step.

12. The method of claim 11 wherein the articulation surface of the orthopaedic implant has a surface skew of from −1 to −3 after the second drag finishing step.

13. The method of claim 1 wherein the articulation surface of the orthopaedic implant comprises metal.

14. The method of claim 13 wherein the articulation surface of the orthopaedic implant comprises a metal selected from a group including a cobalt-chrome alloy and a titanium alloy.

15. The method of claim 1 wherein the orthopaedic implant is selected from a group including:
   a distal femoral component of an orthopaedic knee implant;
   a tibial tray of an orthopaedic knee implant;
   a femoral head of an orthopaedic hip implant;
   a humeral head of an orthopaedic shoulder implant; and
   a glenoid component of an orthopaedic shoulder implant.

16. The method of claim 15 wherein the articulation surface of the orthopaedic implant:
   has an average surface roughness (Sa) of less than 0.1 microns after the second drag finishing step as measured by white light interferometry;
   has a surface skew ($S_{sk}$) of from −1 to −3 after the second drag finishing step as measured by white light interferometry; and
   comprises a metal selected from a group including a cobalt-chrome alloy and a titanium alloy.

17. The method of claim 16 wherein blasting comprises wet blasting with a ceramic bead media having a size in the range of B100 to B125 at a pressure of 30-40 psi to increase the roughness of the surface of the metal orthopaedic implant.

18. The method of claim 17 wherein:
   the first period of time maximum of 40 minutes;
   the second period of time is a maximum of 20 minutes;
   the abrasive media used in the first drag finishing step comprises a plastic composite; and
   the abrasive media used in the second drag finishing step comprises nutshell or corncob based polishing media.

19. A method of treating an articulation surface of an orthopaedic implant comprising the following steps carried out in order:
   a first step of polishing the articulation surface of the orthopaedic implant;
   a second step of blasting the polished surface of the orthopaedic implant; and
   a third step of polishing the blasted surface of the orthopaedic implant, wherein blasting comprises wet blasting with a ceramic bead media having a size in the range of B100 to B125 at a pressure of 30-40 psi to increase the roughness of the surface of the metal orthopaedic implant.

* * * * *